(12) United States Patent
Pernot et al.

(10) Patent No.: US 9,913,756 B2
(45) Date of Patent: *Mar. 13, 2018

(54) ELASTIC BANDAGE HAVING IMPROVED COMPRESSION PROPERTIES

(71) Applicant: LABORATOIRES URGO, Chenove (FR)

(72) Inventors: Jean-Marc Henri Maurice Pernot, Dijon (FR); Serge Lecomte, Dijon (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 130 days.

This patent is subject to a terminal disclaimer.

(21) Appl. No.: 14/425,580

(22) PCT Filed: Sep. 3, 2013

(86) PCT No.: PCT/FR2013/052025
§ 371 (c)(1),
(2) Date: Mar. 3, 2015

(87) PCT Pub. No.: WO2014/033418
PCT Pub. Date: Mar. 6, 2014

(65) Prior Publication Data
US 2015/0238365 A1    Aug. 27, 2015

(30) Foreign Application Priority Data
Sep. 3, 2012  (FR) ...................... 12 58185

(51) Int. Cl.
| A61F 13/00 | (2006.01) |
| A61F 13/02 | (2006.01) |
| A61F 13/06 | (2006.01) |
| D04H 1/498 | (2012.01) |
| D04H 1/541 | (2012.01) |
| B32B 5/02 | (2006.01) |
| B32B 5/06 | (2006.01) |
| B32B 5/24 | (2006.01) |
| B32B 5/26 | (2006.01) |
| B32B 7/12 | (2006.01) |
| D04H 1/4382 | (2012.01) |

(52) U.S. Cl.
CPC .. *A61F 13/00038* (2013.01); *A61F 13/00017* (2013.01); *A61F 13/0273* (2013.01); *A61F 13/06* (2013.01); *A61F 13/069* (2013.01); *B32B 5/022* (2013.01); *B32B 5/06* (2013.01); *B32B 5/245* (2013.01); *B32B 5/26* (2013.01); *B32B 7/12* (2013.01); *D04H 1/4382* (2013.01); *D04H 1/498* (2013.01); *D04H 1/541* (2013.01); *A61F 2013/0028* (2013.01); *B32B 2262/0253* (2013.01); *B32B 2262/0261* (2013.01); *B32B 2262/0276* (2013.01); *B32B 2262/062* (2013.01); *B32B 2262/12* (2013.01); *B32B 2266/0278* (2013.01); *B32B 2307/51* (2013.01); *B32B 2307/726* (2013.01); *B32B 2307/728* (2013.01); *B32B 2535/00* (2013.01)

(58) Field of Classification Search
None
See application file for complete search history.

(56) References Cited

U.S. PATENT DOCUMENTS

| 4,100,324 | A | 7/1978 | Anderson et al. |
| 5,939,339 | A | 8/1999 | Delmore et al. |
| 7,854,716 | B2 | 12/2010 | Schuren et al. |
| 2003/0040691 | A1 | 2/2003 | Griesbach, III et al. |
| 2004/0219854 | A1 | 11/2004 | Groitzsch et al. |
| 2006/0148358 | A1* | 7/2006 | Hall ................ B32B 5/022 442/328 |
| 2008/0269654 | A1 | 10/2008 | Chardon-Bras et al. |
| 2010/0035500 | A1* | 2/2010 | Kimura ............ A61F 13/0273 442/353 |
| 2011/0208101 | A1 | 8/2011 | Keller et al. |
| 2012/0122364 | A1 | 5/2012 | Menczywor |

FOREIGN PATENT DOCUMENTS

| EP | 0878179 A2 * | 11/1998 | ........ A61F 13/069 |
| EP | 2058424 | 5/2009 | |
| EP | 2275062 A2 * | 1/2011 | ........ A61F 13/069 |
| FR | 2890854 | 3/2007 | |
| JP | 2011-184846 | 9/2011 | |
| JP | 2012-012758 | 1/2012 | |
| WO | WO 2007/113430 | 10/2007 | |
| WO | WO 2008/015972 | 2/2008 | |

* cited by examiner

*Primary Examiner* — Kim M Lewis
(74) *Attorney, Agent, or Firm* — Hamre, Schumann, Mueller & Larson, P.C.

(57) ABSTRACT

A compression bandage that is formed by the assembling of a self-adhesive nonwoven based on short conjugate fibers which have been crimped and of an elastic material, the effectiveness of which increases over time. The bandage can be used, alone or in a bilayer compression system, for the prevention or treatment of venous pathologies or lymphedema.

22 Claims, No Drawings

ELASTIC BANDAGE HAVING IMPROVED COMPRESSION PROPERTIES

The present invention relates to a novel compression bandage, formed by the assembling of an elastic material and of a self-adhesive nonwoven based on short conjugate fibers which have been crimped, the effectiveness of which increases over time.

The invention also relates to the use of this bandage, alone or in a bilayer compression system, in particular for the prevention or treatment of venous pathologies or lymphedema.

The use of various compression systems has been known for a long time for treating pathologies of venous origin, such as, for example, venous insufficiency or the treatment of varicose veins and leg ulcers, or also for preventing venous thrombosis or the treatment of lymphedema.

These systems are composed of one or more elastic bandages which apply a pressure to the limb to be treated.

The application of a suitable pressure has a favorable effect:
on the one hand, on the vessels by reducing the diameter of the veins, which results in the acceleration of the blood flow and the reestablishment of the valvular function; and
on the other hand, on the tissues by promoting better oxygenation and resorption of the edema.

In the treatment of chronic wounds and very particularly in that of leg ulcers, the use of a compression system—which makes it possible to reestablish or to promote normal venous circulation—is the reference treatment. This is the only therapy which has proved its effectiveness in treating and preventing the recurrence of wounds of this type.

An effective compression system must make it possible to meet four main objectives.

First, the system must be able to be worn continuously, day and night, for one or more days (for example a week) depending on the pathology, its seriousness or the therapeutic objective (treatment or prevention).

To this end, this system must thus make it possible to simultaneously apply:
on the one hand, a relatively low pressure, known as "resting pressure", when the muscle is relaxed, in order to be comfortable and in particular endurable during the night; and
on the other hand, a relatively high pressure, known as "working pressure", when the muscle is tensed or during movements, in particular during walking.

Secondly, the difference in pressure between resting pressure and working pressure must be sufficient to promote venous reflux.

Thirdly, the values for resting pressure, working pressure and difference in pressure must be stable over time.

Fourthly, the system must be easy and fast to put in place and in complete safety, in order to avoid tourniquet risks, if the pressure applied is too high, or risks of ineffectiveness, if the pressure or the difference in pressure is too low.

In order to achieve these objectives, knitted or woven elastic bandages, known as compression bandages, have been developed.

During its application around a limb, such as the leg, the bandage is stretched; depending on the degree of elongation, it applies, to the leg, a more or less high pressure. This pressure, which is the treatment pressure, depends mainly on two factors, the elongation of the bandage at being put in place and the circumference of the limb on which the bandage is applied.

The elastic compression bandages are thus wound at a given elongation around the leg. During the winding of the bandage, the latter is more or less completely covered over itself. Very often, this covering is 50% in the direction of transverse positioning of the bandage.

It is generally considered that a difference in pressure at 24 hours of between 15 and 25 mm of mercury is necessary in order to reestablish a correct venous flow. However, depending on the pathology, whether it is a treatment on legs without a serious ulcer, a difficult treatment on legs damaged by an edema or a treatment of a mixed arterial and venous ulcer, this range in values can extend from 10 to 35 mm of mercury, indeed even from 10 to 40 mm of mercury.

For ulcers, an applied working pressure at 24 hours of between 20 and 60 mm of mercury, depending on the pathology, is generally targeted.

In the case of the treatment of lymphedema, the important factor is more the applied pressure than the difference in pressure and for this pathology, for example for lymphedema of the leg, a working pressure at 24 hours of greater than 60 mm of mercury, preferably of between 65 and 100 mm of mercury, is targeted.

Manufacturers generally provide tables and ranges of products which, for a given limb diameter, make it possible to determine the pressure to be applied and to choose the appropriate system.

The compression bandages used are categorized by experts in compression into two main categories, depending on the measurement of their elongation.

The classification is based on the measurement of the elongation as defined in the standard EN 14704-1 when the bandage is subjected to a maximum tensile force of 6 N/cm.

The conditions for carrying out the measurement are as follows.

A test specimen of the material to be tested with a width of 50 mm and a length of 250 to 300 mm is cut out and positioned without prestressing in the jaws of an electronic dynamometer (for example, a dynamometer of MTS brand), so as to have a width of 50 mm and a reference working length of 200 mm. The dynamometer stretches the test specimen at a rate of 100 mm/min up to a maximum force of 6 N/cm and then the crosspiece comes back to its initial position at the same return rate of 100 mm/min. This cycle is carried out 5 times and the elongation obtained in the fifth cycle, expressed as percentage, is directly calculated by the device. The operation is repeated on 5 test specimens and the mean value is taken.

1) "Short-Stretch" Bandages

On the basis of this test, taken as reference, a compression bandage is regarded as a "short-stretch" bandage if its elongation is less than or equal to 100%.

These bandages exert a low resting pressure and a high working pressure. They thus have a large difference in pressure, in particular during movements, for example during walking.

However, short-stretch bandages have many disadvantages.

First of all, they are difficult to put in place as small variations in elongation at being put in place generate strong increases or decreases in the pressure achieved and in the difference in pressure obtained. There thus exists a tourniquet risk if the pressure applied is too high or a risk of ineffectiveness if it is insufficient.

A significant decrease over time in the applied pressure and in the difference in pressure between working pressure and resting pressure and often slipping of the compression bandage is also observed.

This results in the need to carry out frequent changes of these bandages and a corresponding increase in the cost of the treatment.

A short-stretch bandage is, for example, sold by Activa under the Actico® name. This bandage is wound over a padding bandage wound beforehand over the leg. The padding is intended to distribute the pressures at the surface of the limb and/or to protect, by its thickness, boney projections and to absorb possible exudates if the bandage is placed on an open wound, for example in the case of leg ulcers.

2) Long-Stretch Bandages

On the basis of the preceding test, taken as reference, a bandage is regarded as a "long-stretch" bandage if its elongation is greater than 100%.

These bandages are easier to put in place as they exhibit a greater extensibility. For this reason, variations in elongation while putting in place do not generate large variations in the applied pressure. The tourniquet risk is low.

On the other hand, these bandages result in low variations in pressure between resting and working and in a low variation in pressure during movements, for example during walking. They prove to be less effective than short-stretch bandages.

They also exhibit a degree of discomfort in the resting position if it is desired to impose a high pressure, hence the need to remove them at night due to the trouble caused.

Long-stretch bandages are, for example, sold by Thuasne, and Smith and Nephew respectively under the Biflex® and Proguide® names.

Multilayer systems have been developed in attempting to overcome these disadvantages.

All the compression systems used today are composed either of a single bandage chosen from these two categories or of the combination of several bandages chosen from these two categories, if necessary in combination with a first padding layer in contact with the skin.

The most effective compression systems sold today are bilayer systems. Said systems are, for example, sold by Laboratoires URGO under the K2® and K2® Lite names. The first bandage (sold under the Ktech® name) is a short-stretch bandage which applies most of the pressure, composed of a layer of padding needled to an elastic network. The second bandage (sold under the Kpress® name) is a self-adhesive long-stretch bandage which applies the additional pressure with respect to the first bandage, in order to obtain the desired pressure, and which is used to keep the first bandage in place. The second bandage is composed of a latex-coated woven. This system makes it possible to optimize the retention of the pressure over time and of the difference in pressures applied.

By working on a better optimization of the effectiveness of these compression systems, in particular in order to improve the retention over time i) of the pressures applied, even when they are high, as in the case of leg lymphedema, and ii) of the difference in pressures between resting pressure and working pressure, the inventors have succeeded in developing a novel elastic bandage with optimized compression properties which allows better retention of the pressures than the most effective systems and the difference in pressure of which no longer decreases over time but, on the contrary, increases.

The assembling of an elastic material with a very specific nonwoven manufactured from short conjugate fibers which have been crimped makes it possible to obtain a novel elastic bandage with noteworthy properties, in particular for the treatment of pathologies of venous origin and lymphedema.

Extensible nonwovens are described in the patent application WO 2008/015972 for their use as compression bandage or taping bandage. The bandages described in this document are nevertheless too weak for their application as compression bandage to be able to be envisaged. This is because a compression bandage has to be sufficiently robust to withstand repeated deformations, rubbing actions and tightening actions for several days, mainly at the heal and malleolus. The compression bandages composed of nonwovens described in the application WO 2008/015972 can be perforated too easily and cannot be used in the field of compression therapy as compression bandages.

These nonwovens correspond neither to long-stretch bandages nor to short-stretch bandages. This is because, if an attempt is made to measure their elongation according to the standard EN 14704-1, which characterizes compression bandages, they break from the first cycle before having reached the maximum tensile force of 6 N/cm.

The applicant has obtained, by the assembling of such a nonwoven and of an elastic material, a product which exhibits noteworthy properties which render it particularly suitable for use in compression therapy.

The product of the invention makes it possible to obtain, with just one bandage, better results—in terms of maintenance of the pressure applied and of the difference in pressure over time—than the compression systems used today and in particular with respect to the bilayer systems which are most effective.

Contrary to what might have been expected, in the light of the weakness of the specific nonwovens, it is found that it is possible to assemble the latter with another material without destructuring them or weakening them even more but also without damaging their properties of extensibility and of self-adhesion.

This novel compression bandage can be used alone or in combination with a second bandage in a bilayer compression system, according to the duration of the treatment and the nature of the pathology to be treated.

The present invention thus relates to a novel compression bandage comprising an elastic material and a nonwoven of crimped fibers obtained from short conjugate fibers, said elastic material and said nonwoven being assembled together and said nonwoven having a grammage of between 70 g/m$^2$ and 300 g/m$^2$.

The fibers are advantageously uniformly crimped in the direction of the thickness of the nonwoven and exhibit a mean radius of curvature of between 10 and 200 micrometers.

The number of crimped fibers at the surface of the nonwoven is preferably greater than 10 crimped fibers/cm$^2$.

In a specific embodiment, a subject matter of the invention is a compression bandage comprising an elastic material and a nonwoven of crimped fibers obtained from short conjugate fibers, said elastic material, and said nonwoven being assembled together, said nonwoven having a grammage of between 70 g/m$^2$ and 300 g/m$^2$, said crimped fibers being uniformly crimped in the direction of the thickness of the nonwoven and exhibiting a mean radius of curvature of between 10 and 200 micrometers, and the number of crimped fibers at the surface of the nonwoven being greater than 10 crimped fibers/cm$^2$.

According to an alternative form, the present invention relates to a self-adhesive compression bandage in which the loops of the nonwoven after needling protrude from the surface of the elastic material, rendering the latter self-adhesive. The bandage can be elastic and self-adhesive without containing latex. Advantageously, the bandage can comprise less than 0.01% by weight of latex or of an adhesive of low adhesion, while being self-adhesive.

Such a self-adhesive bandage is characterized in that it comprises an elastic material and a nonwoven of crimped fibers obtained from short conjugate fibers, said elastic material and said nonwoven being needled together, said fibers being uniformly crimped in the direction of the thickness of the nonwoven and exhibiting a mean radius of curvature of between 10 and 200 micrometers, the number of crimped fibers at the surface of the nonwoven being greater than 10 crimped fibers/cm$^2$, and the bandage exhibits a peel strength at 180° on itself of between 0.02 N/cm and 0.5 N/cm and preferably between 0.025 and 0.05 N/cm.

According to another alternative form, the present invention relates to a compression bandage in which a few loops of nonwoven appear at the surface of the elastic material after needling, so that the slipping of the bandage over itself is reduced.

Such a bandage is characterized in that it comprises an elastic material and a nonwoven of crimped fibers obtained from short conjugate fibers, said elastic material and said nonwoven being needled together, said fibers being uniformly crimped in the direction of the thickness of the nonwoven and exhibiting a mean radius of curvature of between 10 and 200 micrometers, the number of crimped fibers at the surface of the nonwoven being greater than 10 crimped fibers/cm$^2$, and the surface of the elastic material exhibits, after assembling, a dynamic friction coefficient of between 2 and 4 and preferably between 3 and 4.

The nonwoven and the elastic material can be assembled over the whole of their surface, preferably over the whole of the surface of the elastic material; the surface area and the shape of their surfaces can be identical or different. In the case where the bandage is not self-adhesive and is used alone, it will be preferable for the surface of the nonwoven to be greater than that of the elastic material; in particular, a greater length of the nonwoven will be preferred, so as to make possible the terminal attachment of the bandage to itself and then of the winding by virtue of the self-adhesion of the nonwoven to itself.

The nonwoven can have a width identical to that of the elastic material and a greater length, so that the widths of the two materials overlap but that a portion of the length of the nonwoven is not covered by the elastic material in order to facilitate the end of the putting in place of the bandage by the adhesion of the nonwoven to itself.

Nonwovens which can be used in the context of the present invention are described in the patent application WO 2008/015972.

Generally, the fibers which were used to manufacture the nonwoven are preferably conjugate fibers, of polymeric nature and noncontinuous (short).

The conjugate fibers within the meaning of the invention are fibers "having latent crimpability" possessed of an asymmetric or laminated structure which have the property of crimping under the effect of heating. They owe this property to the difference in thermal contraction coefficient of the polymers of which they are composed.

These fibers are advantageously composed of at least two polymers which exhibit a different thermal contraction coefficient. These polymers ordinarily have different softening points or melting points. They can be chosen from thermoplastic polymers, such as, for example: olefinic polymers (in particular $C_{2-4}$ polyolefin polymers, such as low-, medium- and high-density polyethylenes and polypropylenes), acrylic polymers (in particular acrylonitrile polymers having acrylonitrile units, such as acrylonitrile/vinyl chloride copolymers), vinyl acetal polymers (in particular polyvinyl acetal polymers), vinyl chloride polymers (in particular polyvinyl chlorides, vinyl chloride/vinyl acetate copolymers and vinyl chloride/acrylonitrile copolymers), vinylidene chloride polymers (in particular vinylidene chloride/vinyl chloride copolymers and vinylidene chloride/vinyl acetate copolymers), styrene polymers (in particular heat-resistant polystyrenes), polyester polymers (in particular poly($C_{2-4}$ alkylene arylate) polymers, such as polyethylene terephthalate, polytrimethylene terephthalate, polybutylene terephthalate and polyethylene naphthalate polymers), polyamide polymers (in particular aliphatic polyamide polymers, such as polyamides 6, 6-6, 11, 12, 6-10 and 6-12, semiaromatic polyamide polymers or aromatic polyamide polymers, such as polyphenylene isophthalamide, polyhexamethylene terephthalamide and poly(para-phenylene terephthalamide)), polycarbonate polymers (in particular polycarbonates of bisphenol A type), poly(para-phenylene-benzobisoxazole) polymers, polyphenylene sulfide polymers, polyurethane polymers, cellulose polymers (in particular cellulose esters), and the like. These thermoplastic polymers can optionally comprise other copolymerizable units.

When heating of the fibers is carried out with high-temperature steam, according to the preferred embodiment of the nonwoven, preference is given to polymers which are nonadhesive under wet heat (or heat-resistant hydrophobic or water-insoluble polymers), with a softening point or melting point of greater than or equal to 100° C., such as, for example, polypropylene polymers, polyester polymers and polyamide polymers. These polymers make it possible to prevent the bonding of the fibers by melting or softening of the fibers. Preference is very particularly given to aromatic polyester polymers and polyamide polymers, for their excellent stability, their resistance to heat and their ability to form fibers.

According to a preferred form of the present invention, the fibers used are bicomponent fibers. Bicomponent fibers can be composed of polymers of the same chemical family or of polymers of different chemical families, provided that they have different thermal contraction coefficients.

In one embodiment, the short conjugate fibers are bicomponent fibers, the two components making them up being polymers which exhibit a softening point of greater than or equal to 100° C., said polymers being chosen from polypropylene polymers, polyester polymers and/or polyamide polymers and preferably being two different aromatic polyester polymers.

It is preferable for the bicomponent fibers to be composed of two polymers of the same chemical family: for example of a homopolymer and of a copolymer. This is because it is possible to lower the degree of crystallinity of the homopolymer, indeed even to render it amorphous, or to lower its melting point or its softening point by copolymerizing the monomer with another. The difference in melting point or softening point of the two polymers can be, for example, of the order of 5 to 150° C., preferably of 50 to 130° C. and more preferably of 70 to 120° C. The proportion of copolymerizable monomer, with respect to the total amount of monomers, is, for example, of the order of 1 to 50 mol %, preferably of 2 to 40 mol % and more preferably of 3 to 30 mol % (particularly of 5 to 20 mol %). The ratio by weight of the homopolymer to the copolymer can be chosen as a function of the structure of the fibers; it is, for example, in terms of homopolymer (A)/copolymer (B) ratio, of the order of 90/10 to 10/90, preferably of 70/30 to 30/70 and more preferably of 60/40 to 40/60. In a preferred embodiment, the bicomponent fibers are composed of two aromatic polyester polymers and in particular of the combination of a polyalkylene arylate homopolymer (a) and of a polyalkylene arylate copolymer (b). The polyalkylene arylate homopolymer (a) can be a homopolymer of an aromatic dicarboxylic acid (in particular a symmetrical aromatic dicarboxylic acid, such as terephthalic acid or naphthalene-2,6-dicarboxylic acid) and of an alkanediol component (in particular ethylene glycol or butylene glycol). Use is made, for example, of a polymer of the series of the polyalkylene terephthalates, such as polyethylene terephthalate (PET) or polybutylene terephthalate (PBT), and ordinarily a PET with an intrinsic viscosity of the order of 0.6 to 0.7 used in the manufacture of ordinary PET fibers. The polyalkylene arylate copolymer (b) can be obtained from a first monomer used in the preparation of the polyalkylene arylate homopolymer (a) and a second monomer chosen from a dicarboxylic acid, such as an asymmetric aromatic dicarboxylic acid, an alicyclic dicarboxylic acid or an aliphatic dicarboxylic acid, an alkanediol component having a longer chain than the alkanediol of the polyalkylene arylate polymer (a), and/or a diol carrying an ether bond.

It is possible to use just one or to combine several of these second monomers. Among these components, use is preferably made of:

an asymmetric aromatic dicarboxylic acid, in particular isophthalic acid, phthalic acid or 5-sulfoisophthalic acid sodium salt, or an aliphatic dicarboxylic acid, in particular an aliphatic $C_{1-12}$ dicarboxylic acid, such as adipic acid, an alkanediol, in particular 1,3-propanediol, 1,4-butanediol, 1,6-hexanediol or neopentyl glycol, a polyoxyalkylene glycol, in particular diethylene glycol, triethylene glycol, polyethylene glycol or polytetramethylene glycol.

The choice is preferably made, among them, of in particular an asymmetric aromatic dicarboxylic acid, such as isophthalic acid, and a polyoxyalkylene glycol, such as diethylene glycol. The polyalkylene arylate copolymer (b) can optionally be an elastomer having hard alkylene arylate (ethylene terephthalate, butylene terephthalate) segments and having soft segments, for example of (poly)oxyalkylene glycol. In the polyalkylene arylate copolymer (b), the proportion of dicarboxylic acid component intended to lower the melting point or the softening point, with respect to the total amount of dicarboxylic acid component, is, for example, of the order of 1 to 50 mol %, preferably of 5 to 50 mol % and more preferably of 15 to 40 mol %. The proportion of diol component intended to lower the melting point or the softening point, with respect to the total amount of diol component, is, for example, at most 30 mol % and preferably at most 10 mol %, for example of the order of 0.1 to 10 mol %.

The cross section (section perpendicular to the direction of the length of the fibers) of the bicomponent fibers is not limited to the round shape (the ordinary shape of solid fibers) and to the modified shapes (flat, elliptical, polygonal, 3- to 14-foliated, T-shaped, H-shaped, V-shaped, "dog bone"-shaped (i-shaped), and the like) but can also be a hollow section. However, normally the round section is chosen.

Mention may be made, for the transverse structure of the bicomponent fibers, of the phased structures formed by a plurality of polymers, such as, for example, the structures of core-shell, islands and sea, mixed, parallel (side by side or multilayer laminate), radial (radial laminate), hollow radial, block or random types. Preference is given, among these structures, for a more spontaneous development of the thermal crimping, to a structure of eccentric core-shell type or of parallel type. In the case of bicomponent fibers of core-shell type and for example of eccentric core-shell type, the core can be composed of a polymer of the vinyl alcohol family, such as an ethylene/vinyl alcohol copolymer or a polyvinyl alcohol, or of a thermoplastic polymer with a low melting point or low softening point, for example a polystyrene or a low-density polyethylene, provided that it allows the crimping by the fact of having a difference in thermal contraction coefficient with the polymer constituting the shell.

In a specific embodiment, the bicomponent fibers have a structure of side by side type and are composed of a first polymer which is a polyethylene terephthalate and of a second polymer which is a copolymer of an alkylene arylate with isophthalic acid and/or diethylene glycol.

The mean count of the short conjugate fibers, in particular bicomponent fibers, can, for example, be between 0.1 and 50 dtex, preferably between 0.5 and 10 dtex and more preferably between 1 and 5 dtex (particularly between 1.5 and 3 dtex). If the count is too fine, not only are the fibers difficult to manufacture but there is a risk that they will lack strength. Furthermore, in the crimping stage, it is difficult to obtain beautiful coil-shaped crimps. If the count is too large, the fibers become stiff and make it difficult to develop a sufficient crimping.

The mean length of the short conjugate fibers before the crimping can, for example, be between 10 and 100 mm, preferably between 20 and 80 mm and more preferably between 25 and 75 mm (particularly between 40 and 60 mm). If the fibers are too short, apart from the difficulty in forming the web of fibers, the entangling of the fibers is insufficient in the crimping stage and it is difficult to guarantee good properties of strength and of extensibility. If the fibers are too long, not only does it become difficult to form a web of fibers of uniform grammage but the fibers become excessively entangled during the formation of the web, to the point of mutually hindering each other at the time of the crimping and of preventing the development of the extensibility. Furthermore, in the invention, the choice of the fiber length within the abovementioned range makes it possible for a portion of the crimped fibers at the surface of the nonwoven to slightly emerge from said surface of the nonwoven and thus to improve the self-adhesiveness of the nonwoven, which will be touched upon later.

In one embodiment, the mean count of the short conjugate fibers is between 1 and 5 dtex, preferably between 1.5 and 3 dtex, and the mean length of the short conjugate fibers is between 10 and 100 mm and preferably between 40 and 60 mm.

The application of a heat treatment to these conjugate fibers has the effect of developing the crimping and of imprinting on them crimps in relief having the shape of coils (spiral shaped or "coil spring"-shaped). The mean radius of curvature of the crimped fibers within the meaning of the invention corresponds to the mean radius of curvature of the circles formed by the loops of the coils of the crimped fibers; it can be between 10 and 200 microns, for example between 10 and 250 microns, preferably between 20 and 200 microns, preferentially between 50 and 160 microns and more preferentially between 70 and 130 microns.

The mean radius of curvature of the crimped fibers can be determined by electron microscopy according to the following method. A micrograph (magnification ×100) of a section of nonwoven is taken with a scanning electron microscope (SEM). Among the fibers appearing on the photograph, the fibers forming at least 1 spiral turn (coil) are selected and their radius of curvature is determined as the radius of the circle drawn along the spiral (radius of the circle when the crimped fiber is observed in the direction of the axis of the coil). When the fiber forms an elliptical spiral, the radius of curvature is determined as the half-sum of the great and small diameters of the ellipse. In order to exclude the fibers which have developed an insufficient coil-shaped crimping and the fibers which appear elliptical because of an oblique observation of the spiral, the procedure has been restricted to the elliptical fibers with a ratio of great to small diameters of between 0.8 and 1.2. The measurement is carried out, on the SEM image, of an arbitrary section of nonwoven and the mean is determined with regard to a population of fibers n=100.

When the crimping is carried out with high-temperature steam, the nonwoven according to the invention has the characteristic that the crimping of the conjugate fibers oriented approximately parallel to the planar direction is developed in an almost uniform fashion in the direction of the thickness. In a section of nonwoven taken in the direction of the thickness, among the domains delimited by a division into three equal parts in the direction of the thickness, the number of fibers forming at least 1 spirally wound crimp turn is, for example, in the central part (internal layer), from 5 to 50 per 5 mm (length in the planar direction) and 0.2 mm (thickness), preferably from 10 to 50 per 5 mm (planar) and 0.2 mm (thickness) and more preferably from 20 to 50 per 5 mm (planar) and 0.2 mm (thickness).

As the majority of the crimped fibers have their axis oriented in the planar direction and as the number of crimps is uniform in the direction of the thickness, the nonwoven displays a high extensibility (without comprising rubber or elastomer) and good operational strength (without comprising adhesives).

In the present description, the term "domains delimited by a division into three equal parts in the direction of the thickness" is understood to mean the different domains obtained when the nonwoven is cut into three equal slices oriented perpendicularly to the thickness.

In the nonwoven, uniformity of the crimping in the direction of the thickness can be defined by the fiber incurvation ratio. The term "fiber incurvation ratio" is understood to mean the L2/L1 ratio of the length of the two-dimensionally stretched fiber L2 to the distance L1 of the two ends of the fiber in the crimped state. This fiber incurvation ratio (in particular in the central domain in the direction of the thickness) is, for example, of the order of at least 1.3 (for example of 1.35 to 5), preferably of 1.4 to 4 (for example of 1.5 to 3.5) and more preferably of 1.6 to 3 (particularly of 1.8 to 2.5).

When the fiber incurvation ratio is measured on the basis of electron micrographs of sections of the nonwoven, the fiber length L2 does not correspond to the length of the fiber which would be obtained if the crimped fiber were stretched and rectilinearized three-dimensionally. It corresponds to the fiber length on a photograph which is obtained when the fiber appearing crimped is stretched and rectilinearized two-dimensionally on the photograph. In other words, the fiber length on the photograph which is measured according to the invention is lower than the real fiber length.

When the development of the crimping is approximately uniform in the direction of the thickness, the fiber incurvation ratio is also uniform in the direction of the thickness. The uniformity of the fiber incurvation ratio can be evaluated by comparing, in a section taken in the direction of the thickness, the fiber incurvation ratios obtained in the different layers delimited by a division into three equal parts in the direction of the thickness. Thus, in a section taken in the direction of the thickness, the fiber incurvation ratios obtained in the different domains delimited by the division into three equal parts in the direction of the thickness all lie in the abovementioned range and the ratio of the minimum value to the maximum value of the fiber incurvation ratio in the different domains (ratio of the domain where the fiber incurvation ratio is minimum to the domain where it is maximum) is, for example, of the order of at least 75% (for example, of 75 to 100%), preferably of 80 to 99% and more preferably of 82 to 98% (particularly of 85 to 97%).

According to one embodiment, the nonwoven exhibits, in a section taken in the direction of the thickness, a fiber incurvation ratio of greater than or equal to 1.3 in each of the domains delimited by a division into three equal parts in the direction of the thickness and the ratio of the minimum value to the maximum value of the fiber incurvation ratio in the different domains is greater than 75%.

As concrete method for measuring the fiber incurvation ratio and its uniformity, it is possible to apply the method which consists in taking a micrograph of the section of the nonwoven with an electron microscope and in measuring the fiber incurvation ratio on domains chosen within the different domains of the division into three equal parts in the direction of the thickness. The measurement is carried out, in each of the upper (front domain), internal (central domain) and lower (back domain) layers, on domains which, in the direction of the length, are at least 2 mm and, in the direction of the thickness, are positioned close to the center of each layer and have the same thickness from one domain to the other. Furthermore, these measurement domains are parallel in the direction of the thickness and are defined so that each includes at least 100 fragments of fibers allowing the measurement of their incurvation ratio (of the order preferably of at least 300 and more preferably of 500 to 1000). After having defined these measurement domains, the fiber incurvation ratio of all the fibers located in the domain is measured and the mean value with regard to each measurement domain is calculated, and then the uniformity of the fiber incurvation ratio is calculated by comparing the domain showing the greatest mean value and the domain showing the smallest mean value.

The fiber incurvation ratio and its uniformity can be measured according to the following methodology. A micrograph (magnification ×100) of a section of nonwoven is taken with an electron microscope and, in a portion where the fibers appear on the photograph, the thickness is divided into three equal domains (front, internal and back layers) and, close to the center of each domain, measurement domains of at least 2 mm in the direction of the length and comprising at least 500 fragments of fibers which can be measured are defined. The inter-end distance (shortest distance) between the two ends of the fiber, on the one hand, and the fiber length (length of the fiber on the photograph), on the other hand, are measured on these domains.

Specifically, when one fiber end emerges at the surface of the nonwoven, it is selected as is as end for measurement of the inter-end distance; when one fiber end dives into the nonwoven, the diving limiting portion in the nonwoven (end on the photograph) is selected as end for measurement of inter-end distance.

Among the fibers imaged, those on which it is not possible to isolate a continuity of at least 100 µm are excluded from the measurement. The fiber incurvation ratio is calculated as the L2/L1 ratio of the fiber length L2 to the inter-end distance L1 of the fibers. The mean on each of the front, internal and back layers of the division into three equal parts in the direction of the thickness is then calculated. Finally, the uniformity of the fiber incurvation ratio in the direction of the thickness is calculated from the ratio of its maximum and minimum values in the different layers.

The principle of the method for measurement of the fiber length is illustrated in FIGS. 4-a and 4-b of the patent application WO 2008/015972.

FIG. 4-(a) illustrates the case of a fiber, one end of which emerges at the surface and the other end of which dives into the nonwoven. The inter-end distance L1 is in this instance the distance from one end of the fiber as far as the diving limiting portion in the nonwoven. Furthermore, the fiber length L2 is the length obtained when the portion of the fiber which can be observed (portion ranging from the end of the fiber as far as the diving portion in the nonwoven) is stretched two-dimensionally on the photograph.

FIG. 4-(b) illustrates the case of a fiber, both ends of which dive into the nonwoven. The inter-end distance L1 is in this instance the distance of the two ends of the portion emerging at the surface of the nonwoven (ends on the photograph). Furthermore, the fiber length L2 is the length obtained when the fiber in the portion emerging at the surface of the nonwoven is stretched two-dimensionally on the photograph.

For coil-shaped crimped fibers, the mean pitch of the coil is, for example, of the order of 0.03 to 0.5 mm, preferably of 0.03 to 0.3 mm and more preferably of 0.05 to 0.2 mm.

The nonwoven can also comprise fibers which are not bicomponent fibers. Mention may be made, among these additional monocomponent fibers, for example, of the fibers of polymers already mentioned above but also cellulose fibers, such as, for example, natural fibers (wood wool, sheep wool, silk, hemp), semisynthetic fibers (in particular acetate fibers, such as triacetate fibers) or regenerated fibers (rayon, lyocell). The mean count and the mean length of the monocomponent fibers are preferably identical to those of the bicomponent fibers. It is possible to use just one type or to combine several types of these monocomponent fibers. Among these monocomponent fibers, preference is given in particular to regenerated fibers, such as rayon fibers, to semisynthetic fibers, such as acetate fibers, to polyolefin fibers, such as polypropylene or polyethylene fibers, to polyester fibers and to polyamide fibers.

It is preferable to combine, with bicomponent fibers of a chemical family (for example polyester family), monocomponent fibers of the same chemical family.

The ratio by weight of the bicomponent fibers to the monocomponent fibers is, for example, of the order of 80/20 to 100/0 (for example of 80/20 to 99/1), preferably of 90/10 to 100/0 and more preferably of 95/5 to 100/0.

The nonwoven which makes up the bandage of the invention is advantageously devoid of elastomeric fibers. Such elastomeric fibers are generally long filaments or fibers obtained from thermoplastic materials, such as polyurethane, polyamide, styrene copolymers or polyester. They are generally obtained by the melt blown process and generally have a length of greater than 100 mm. The nonwovens are advantageously devoid of long fibers positioned in the longitudinal direction of the bandage.

The nonwoven can also comprise additives, such as stabilizing agents, UV screening agents, photostabilizers, antioxidants, antibacterials, deodorizing agents, fragrances, colorants, fillers, antistatic agents, flame retardants, plasticizers, lubricants or crystallization retardants. It is possible to use just one or several of these additives. These additives can both be supported at the surface of the fibers and present inside the fibers.

In order to be able to obtain a compression bandage with the desired properties, the choice will be made—among the nonwovens produced from the fibers and polymers described above—of a nonwoven which exhibits a grammage of between 70 and 300 $g/m^2$, preferably between 80 and 200 $g/m^2$ and more preferably between 90 and 150 $g/m^2$.

The grammage can be measured according to the standard EN 9073-1.

An excessively low grammage makes assembling impossible as there is a risk of the excessively weak product being destroyed during assembling and an excessively high grammage does not make it possible to obtain the desired compromise between the extensibility, tearability and self-adhesion characteristics.

The other mechanical properties of the nonwoven will preferably be as follows.

The thickness of the nonwoven will advantageously be between 0.25 and 5 mm, preferably between 0.4 and 2.5 mm and very particularly between 0.5 and 1.5 mm. The thickness can be measured according to the standard EN 9073-2.

The lengthening of the nonwoven, that is to say its elongation at break, will be, in the longitudinal direction, advantageously of between 60 and 200% and preferably between 90 and 130% and, in the transverse direction, of between 70 and 200% and preferably between 60 and 160%. The longitudinal and transverse lengthening can be measured according to the standard EN 9073-3. The test of this standard consists in measuring the elongation at break, expressed as percentage, which corresponds to the value of the lengthening. The test conditions in the longitudinal direction are as follows.

A sample of the material to be tested (for example the nonwoven) with a length of 300 mm and with a width of 50 mm is subjected to a tensile test using an electronic dynamometer in which the crosspiece moves at a rate of 100 mm/mn. The space between the jaws is adjusted to 200 mm and the width is that of the test specimen, i.e. 50 mm. The dynamometer automatically stops when the sample breaks and the device records the elongation at break. The test is repeated on three samples and the mean value is taken.

In the transverse direction, the measurement is carried out in an identical fashion, the length between the jaws being adapted to the width of the material to be tested; for example, with a material with a width of 10 cm, the length of the sample between the jaws is 6 cm.

The elasticity of the nonwoven, as defined in the standard EN 14704-1, that is to say its elastic recovery after an elongation of 30%, is preferably greater than or equal to 70% (for example between 70 and 100%) and preferably between 80 and 95%.

The principle of the standard EN 14704-1 is based on the measurement of the elastic recovery is as follows. The conditions of the measurement are as follows.

A test specimen (for example of compression bandage or nonwoven) with a width of 50 mm and a length of 200 mm is inserted into the jaws of an electronic dynamometer, which will carry out a series of 5 cycles, up to an elongation of 30%, of "loading-unloading" tension at a rate of 100 mm/mn. The elongation recovered, obtained in the fifth cycle, expressed as percentage, as defined in the standard, is automatically measured by the dynamometer. The measurement of the elastic recovery, expressed as percentage, is calculated according to the formula defined in the standard on the basis of this recovered elongation. The operation is repeated on three test specimens and the mean value is taken.

In the context of the present invention, a material is regarded as elastic if its elastic recovery is greater than or equal to 70%.

The self-adhesion of the bandage according to the invention is obtained by virtue of the presence of numerous fibers in the partially free state at the surface of the nonwovens, the surface fibers mutually entangling at the time of the superimposition of the bandage on itself. In order to obtain this self-adhesion property without detrimentally affecting the tearability and extensibility properties, the number of crimped fibers, in particular in the form of a coil or loop, at the surface of the nonwoven is advantageously greater than 10 crimped fibers/cm$^2$ and preferably between 10 and 50 crimped fibers/cm$^2$. For the preparation of a compression bandage, preference will be given to a number of crimped fibers at the surface of the nonwoven of between 10 and 35 crimped fibers/cm$^2$.

According to a specific embodiment, the nonwoven is composed of side by side bicomponent fibers based on aromatic polyester polymers, the nonwoven has a grammage of between 90 and 150 g/m$^2$, and the number of crimped fibers at the surface of the nonwoven is between 10 and 35 crimped fibers/cm$^2$.

The number of crimped fibers at the surface of the nonwoven can be determined as follows.

A micrograph (magnification ×100) of the surface of the nonwoven is taken with an electron microscope and the number of crimped fibers (fibers making at least one loop-shaped spiral turn or coil turn which are formed at the surface of the nonwoven) is counted over a unit area of 1 cm$^2$ of surface of imaged fibers. The measurement can be carried out at five arbitrary points and the mean number of looped fibers, rounded to the nearest unit, is calculated.

The characterization of the self-adhesion of the nonwoven or of the bandage is evaluated by the measurement of the peel strength of a sample folded over itself. This peel strength varies between 0.02 and 0.5 N/cm and preferably between 0.025 and 0.1 N/cm.

The test for characterizing the self-adhesion consists in measuring the peel strength at 180° of a sample of material using an electronic dynamometer. This peel strength represents the value of the self-adhesion of the material. The conditions for carrying out the measurement are advantageously as follows.

A sample of material with a length of 60 cm and a width of 5 cm is folded over itself while leaving free the ends which will be used to attach it in the jaws of the electronic dynamometer. The two faces are brought into contact under the pressure of a weight equivalent to 1 kgf/cm. Peeling is carried out by adjusting the dynamometer to a rate of 300 mm/mn. The dynamometer directly gives the peel strength, expressed in N/cm. The test is repeated on 3 samples and the mean value is taken.

An elastic material is understood to mean any material which exhibits, after a length of 30%, an elastic recovery, as defined in the standard EN 14704-1, of greater than or equal to 70%. An elastic material within the meaning of the invention is not a nonwoven of crimped fibers as described above.

This elastic material can make it possible to adapt, according to the pathology targeted or the uses envisaged, the absorption, dampening, conformability, stiffness or occlusivity properties of the compression bandage.

The elastic material can be chosen from textile materials, cellular materials, films or their combinations.

Among textile materials, materials based on synthetic or natural fibers can be used. Mention may be made of wovens, nonwovens, knitwear, 3D knitwear and their combinations.

Any type of nonwoven can be used as elastic material, with the exception of the nonwovens based on short conjugate crimped fibers used for the other assembling layer.

It will be preferable to use materials which make it possible to improve the dampening or absorption properties and very particularly cellular materials and 3D knitwear.

Mention may be made, among the cellular materials, of hydrophobic or hydrophilic foams, for example based on polyurethane or based on olefins. Preference will in particular be given, in the case of the treatment of leg ulcers, to absorbent hydrophilic foams, such as, for example, the foam sold under the reference MCF.03 by Advanced Medical Solution (AMS). Mention may be made, as non-absorbent foam, for example, of the olefin-based foams sold by Alveo under the Alveolit® name.

According to one embodiment, the elastic material is a hydrophobic or hydrophilic foam, preferably a hydrophilic polyurethane foam, or a 3D knitwear.

Use may be made, as films, of any flexible polymeric film, for example based on polyurethane, polyolefin, polyamide, polyester or polyvinyl chloride.

Mention may be made, among 3D knitwear, for example, of the products sold by Louis Vuidon.

The elastic material can optionally comprise active agents which contribute to improving the healing of the leg ulcer or which make it possible to reduce the pain or the edema, or also antibacterial agents.

According to an alternative embodiment, in the case of a textile material, it will be possible to introduce, into the elastic material, antibacterial fibers, for example silver fibers, or to impregnate the elastic material with an antibacterial, for example triclosan.

The compression bandage according to the invention is produced by assembling the elastic material and a nonwoven chosen from those as defined above.

Assembling is understood to mean any means which make it possible to bond the nonwoven and the elastic material together, with the result that their simple superimposition cannot be regarded as assembling.

Varied textile technologies, such as, for example, sewing, needling, ultrasound welding, laminating or setting using an adhesive can be used to carry out this assembling.

According to one embodiment, the nonwoven and the elastic material are assembled by needling, with an adhesive or by ultrasound.

These technologies will be chosen according to the nature of the materials (nonwoven and elastic material) to be assembled, in particular their resistance to temperature and their mechanical strength.

This assembly will be carried out so as not to detrimentally affect the self-adhesion and extensibility properties of the nonwoven and to guarantee the absence of delamination of the product over time.

In order to guarantee the absence of delamination of the product, care will be taken that the delamination strength between the nonwoven and the elastic material is greater than 10 cN/cm and preferably greater than 25 cN/cm.

The principle of the measurement of the delamination is based on the method commonly known as T-type delamination in which the force necessary to delaminate the materials making up the compression bandage is measured. This delamination force can be measured according to the following protocol. A test specimen is cut out from a compression bandage with a width of 50 mm and a length of 300 mm. The end of this test specimen is delaminated manually over a length of 1 to 3 cm, so as to fix each delaminated end of the bandage in the jaws of a dynamometer. The measurement is carried out so that there is an angle of 90° between the compression bandage and the end of the bandage delaminated beforehand. The delamination force is measured using the electronic dynamometer in which the crosspiece is movable and moves at the rate of 300 mm/min. The dynamometer directly records this measured force, which is expressed in cN/cm. The test is repeated on 3 test specimens and the mean value is taken.

Preference will very particularly be given to assembling by needling which makes it possible to obtain a greater number of categories of compression bandages than the other techniques.

This is because, by varying the nature or characteristics of the elastic material, for example its thickness, and the needling parameters (number of needles, depth of needling, and the like) it is possible to obtain a bandage in which the loops of the nonwoven emerge at the surface of the elastic material on the side opposite the specific nonwoven.

Two categories of bandages are thus obtained: self-adhesive bandages and bandages which exhibit slight catching, when they are wound over themselves.

According to one embodiment, the elastic material and the nonwoven are needled and the bandage exhibits a peel strength at 180° on itself of between 0.02 and 0.5 N/cm and preferably between 0.025 and 0.05 N/cm.

Compression bandages are thus obtained which are highly advantageous as they are self-adhesive, by virtue of the entangling of the loops of the nonwoven and of those which project from the surface of the elastic material, without it being necessary to use latex or an adhesive.

In the case of the bandages which exhibit slight catching, only a few loops pass through the elastic material and show at the surface of the latter during the needling. These bandages are characterized by a surface of the elastic material after assembling which exhibits a dynamic friction coefficient of between 2 and 4 and preferably between 2 and 3. According to one embodiment, the elastic material and the nonwoven are needled and the surface of the elastic material exhibits, after assembling, a dynamic friction coefficient of between 2 and 4 and preferably between 2 and 3.

The dynamic friction coefficient characterizes the ability of a surface to slide over itself. The measurement of the dynamic coefficient is based on the principle described in the standard EN ISO 8295. It consists in measuring the force for moving over a large plate, using an electronic dynamometer, a 200 g square steel block with a length of 63.5 mm and a width of 63.5 mm, which block is covered with the compression bandage with the elastic material side towards the outside, which slides over the large plate which itself is also covered over the whole of its surface with the compression bandage in the same way. The two surfaces of the elastic material are thus in contact with one another and the block is drawn at the rate of 150 mm/min by the dynamometer. The bandages are adhesively bonded to the steel block and to the plate using double-sided adhesive tape. The block is connected by a cable to the force sensor of the dynamometer. The measurement of the dynamic friction coefficient is the ratio of the tensile force, expressed in Newtons, measured by the dynamometer, to the weight of the block, expressed in Newtons, i.e. 1.96 N as defined in the standard. The measurement is carried out on three samples cut out from the same bandage and the mean value is taken.

The compression bandage of the invention can be manufactured by a manufacturing process in which the elastic material and the nonwoven of crimped fibers are assembled together by needling, preferably without prestressing the nonwoven of crimped fibers, that is to say without stretching the nonwoven prior to the needling.

Use may be made, as needling machine, of a Fehrer machine having a board comprising between 800 and 3000 needles per linear meter.

The choice will preferably be made of an output rate on the needling line of between 0.5 and 25 meters/minute, a length of penetration of the needles between 8 and 25 mm and a needling density of between 10 and 50 punches/cm$^2$. According to an embodiment, the length of penetration of the needles is between 10 and 25 mm.

For short treatment times, for example of 1 to 3 days, or from a preventive perspective, use is often made of non-self-adhesive bandages which are fixed at the end of winding over themselves using an adhesive tape or clips. One of the problems of these bandages is that, during use, the turns of the bandage slide over themselves, which results in slackening them and in them sliding with respect to one another, and the bandage ends up by sliding over the leg and falling off.

With a bandage which exhibits, as characteristic, a dynamic friction coefficient like that of the surface of the elastic material after assembling defined above, this phenomenon of sliding of the turns over themselves or turns over turns is reduced or eliminated, and the effectiveness of bandages of this type is improved.

All the characteristics of bandages can be used alone or in multilayer systems, in particular bilayer systems, according to the desired purpose.

According to a preferred embodiment, in order to promote precise positioning in place by the nursing personnel, the compression bandage will be provided with a calibration means. This calibration means can be visual, such as, for example, a group of pictograms, uniformly spaced, printed on the bandage or produced by means of a calibration system. Information on the recommended elongations when the bandage is put in place can be provided with the calibration means. The calibration can be carried out by the nursing personnel in the form of a stencil. This type of stencil or the explanations necessary to manufacture it can be incorporated in the packaging of the bandage. A kit comprising several bandages of different compositions, of different widths, of different lengths and/or having different calibrations in order to apply specific pressures can be used.

When the kit is indicated for the treatment of leg ulcers, it can in addition comprise one or more dressings intended to be put in place over the wound before the bandage is put in place.

In addition to the use in the treatment and prevention of pathologies of venous origin, in particular leg ulcers, or the treatment of lymphedema, in particular leg lymphedema for which it is necessary to apply very high pressures, the products according to the invention, preferably when they are self-adhesive, can be used in any application where the retention of an applied pressure is important.

Mention may thus be made of the treatment and prevention of traumatic pathologies or joint, tendon, bone or muscle injuries.

Another subject matter of the invention is the use of a compression bandage as described above in a bilayer compression system and in particular as first layer.

The compression bandage of the invention makes it possible to obtain moderate, indeed even high, working pressures which are maintained over time. To date, it has been impossible to maintain high working pressures which are stable over time with short-stretch bandages.

The performance of the compression bandages of the invention can be evaluated in terms of working and resting pressures applied and of difference in pressure, over time, by using the in vitro test device and method described in the patent application WO 2007/113430, page 17, line 26, to page 19, line 18.

According to this method, the bandage is put in place around a cylinder with a total cover of 100% and then the circumference of the cylinder is continuously varied at a set rate between a "resting" position (smallest diameter) and a "working" position (greatest diameter), in order to mimic muscle contraction. Pressure sensors measure, over time, the values of the resting pressures and working pressures.

The time difference between the working pressure and resting pressure measurements is 5 seconds and the frequency of the measurements of these two successive parameters is 0.2 Hz.

In order to test the compression bandages according to the invention, it is possible to determine the elongation at the putting in place of the bandage as a function of the desired working pressure, for example using the tension/break curve as defined in the standard EN 9073-3.

In order to appropriately put the bandage in place, the bandages can be calibrated using a stencil, as described in the patent application WO 2007/113430, page 13, line 18, to page 14, line 6. If necessary, the value of the percentage of elongation at being put in place can be refined by a few successive tests.

The "Max. Pressure at T0" value corresponds to the first working pressure recorded immediately after putting in place and "Delta at T0" corresponds to the difference in pressure between the first working pressure and the first resting pressure which are recorded immediately after putting in place. The "Max. Pressure at T24" and "Delta at T24" values correspond to the measurements recorded 24 hours after putting in place. The difference in each of these two values between T0 and T24 hours, "Max. Pressure (T0-T24)" and "Delta (T0-T24)", is calculated.

The loss in working pressure at 24 hours, "Loss in Max. Pressure T24", with respect to the working pressure at being put in place, is also calculated by determining the ratio of the variation "Max. Pressure (T0-T24)" to the "Max. Pressure at T0".

The compression bandages according to the invention advantageously exhibit a working pressure at 24 hours ("Max. Pressure at T24") which varies from 30 to 100 mm of mercury, for example from 40 to 80 mmHg or from 60 to 100 mmHg.

In addition, the compression bandages of the invention exhibit an excellent retention of the pressure applied at being put in place after 24 hours.

The large fall in this value is generally of the order of 25 to 40% after 24 hours for the short-stretch compression bands of the prior art and of the order of 20 to 25% for the two-layer systems of the prior art. Thus, the "Max. Pressure (T0-T24)" value of the compression bandages of the present invention is advantageously less than 20%, for example between 10 and 15%, indeed even less than 5%.

Compression bandages of the invention such that the pressure at 24 hours ("Max. Pressure at T24") is greater than 60 mm of mercury and preferably between 70 and 100 mm of mercury are of use in the treatment of lymphedema, in particular leg lymphedema.

The value of the differences in pressure at 24 hours ("Delta at T24") of the bandages of the invention is advantageously between 10 and 40 mm of mercury, for example between 30 and 35 mm of mercury.

The bandages of the invention exhibit, entirely unexpectedly, a negative difference between the Delta after being put in place and the Delta at 24 hours ("Delta (T0-T24)"). This result is all the more remarkable as it is obtained by a slower fall in the working pressure, "Max. Pressure", than that in the resting pressure. The compression bandages according to the invention are thus the first to improve their effectiveness over time.

The bandages of the invention make it possible to treat mixed arterial and venous ulcers by applying low working pressures of the order of 30 to 35 mm of mercury and by maintaining a difference in pressure ranging from 5 to 20 mm of mercury.

The bandages of the invention can have an elongation of greater than 100%, in particular when it is measured according to the standard EN 14704-1. Thus, the bandages of the invention can exhibit both the elasticity of a long-stretch bandage of the prior art and a very high difference in pressure at 24 hours characteristic of a short-stretch bandage of the prior art.

The bandages of the invention can have an elongation of less than 100%, in particular when it is measured according to the standard EN 14704-1.

The compression bandage of the invention is advantageously such that, at a working pressure, "Max. Pressure at T0", equivalent to that of another compression system of the prior art, the loss in pressure at T24 is reduced, which makes it possible to change the bandage less often.

Various examples of bandages in accordance with the present invention will now be given.

EXAMPLES

Different materials were used to manufacture bandages.
1. Materials Used
a) Elastic Materials
The materials used are commercial products, the names or references of which are as follows, and they are shown in table 1 in abbreviated form:
hydrophilic polyurethane foams sold by AMS with a thickness of 4.5 mm (abbreviated to 4.5 mm foam) and with a thickness of 2.5 mm (abbreviated to 2.5 mm foam),
3D knitwear, sold by Louis Vuidon under the references 9315 and 9031 (abbreviated to Knitwear 9315 and Knitwear 9031).
b) Nonwoven
The examples use a self-adhesive nonwoven, based on crimped asymmetric bicomponent fibers, manufactured according to the teaching of the patent application WO 2008/015972, which carries the reference SJJ 146 from Kuraray.

The fiber used is a fiber of the side by side type, based on polyester, the reference of which from Kuraray is PN-780.

This nonwoven exhibits the following properties and characteristics:

|  | Nonwoven B |
|---|---|
| Grammage (standard EN 9073-1) | 134 g/m$^2$ |
| Thickness (standard EN 9073-2) | 1.14 mm |
| Elasticity (standard EN 14704-1) | 87% |
| Longitudinal lengthening (standard EN 9073-3) | 104% |

-continued

|  | Nonwoven B |
|---|---|
| Transverse lengthening (standard EN 9073-3) | 65% |
| Self-adhesion* | 0.03 N/cm |
| Number of crimped fibers at the surface of the nonwoven** | 27/cm$^2$ |

*measured according to the method described above
**measured according to the method described above 2. Assembling Different assembling techniques were used to manufacture the bandages: needling or application of an adhesive by points.

a) Conditions for Assembling by Needle

The tests on laminating by needling were carried out on a Fehrer needling machine using a board comprising 2500 needles per linear meter.

Two different types of needling were employed to prepare the compression bandages of the invention.

Needling 1

The implementational conditions on the needling 1 line are as follows:

Output rate on the needling line: 1 meter/minute
Penetration of the needles: 10 mm for example 1 and 13 mm for example 2
Needling density: 50 punches/cm$^2$ The elastic material and the nonwoven are combined before needling 1 without prestressing the nonwoven.

Needling 2

The implementational conditions on the needling 2 line were as follows:

Line speed=1 m/min
Penetration of the needles: 13 mm
Needling density: 50 punches/cm$^2$ The elastic material and the nonwoven were combined before needling 2 without prestressing the nonwoven.

b) Conditions for Assembly by Application of Adhesive by Points Under Hot Conditions with an Engraved Cylinder Assembling with an adhesive was used when the application temperature of the adhesive necessary in order to deposit it is compatible with the nonwoven. When the bandage comprises a supplementary layer, the surface of the has to be sufficiently even for the adhesive to be able to be uniformly distributed.

The product was produced on a Cavimelt apparatus for laminating by an engraved cylinder (left-hand part).

Cylinder used=cylinder No. 6 Engraving Net 1
Test conditions of the apparatus:
Operating speed=2 m/min
Rolling slot=0.3 mm
Rolling cylinder pressure=3 bar
Anvil roll pressure=2.5 bar
Heating temperature=188° C.
Temperature of the adhesive=180° C.

The supplementary layer of foam was spread with adhesive and then the nonwoven was laminated. The hot melt adhesive used was a polyester adhesive having the Griltex D 2116 E® trade name from EMS.

All of the bandages produced and the assembling techniques are collated in table 1.

TABLE 1

| Example | Elastic material | Assembling |
|---|---|---|
| 1 | 4.5 mm foam | Needling 1 |
| 2 | 4.5 mm foam | Needling 1 |

TABLE 1-continued

| Example | Elastic material | Assembling |
|---|---|---|
| 3 | 4.5 mm foam | Adhesive |
| 4 | 2.5 mm foam | Needling 2 |
| 5 | Knitwear 9031 | Needling 2 |
| 6 | Knitwear 9315 | Needling 2 |

3. Performance of the Compression Bandages

The performance of the compression bandages of examples 1 to 6 were evaluated in terms of working and resting pressures applied and of difference in pressure over time.

The in vitro testing device and method described in the patent application WO 2007/113430, page 17, line 26, to page 19, line 18, was used.

According to this method, the bandage is put in place around a cylinder with a total cover of 100% and then the circumference of the cylinder is continuously varied at a set rate between a "resting" position (smallest diameter) and a "working" position (greatest diameter), in order to mimic muscle contraction. Pressure sensors measure, over time, the values of the resting pressures and working pressures.

The time difference between the working pressure and resting pressure measurements is 5 seconds and the frequency of the measurements of these two successive parameters is 0.2 Hz.

In order to test the compression bandages according to the invention, the elongation at the putting in place of the bandage was determined as a function of the desired working pressure, for example using the tension/break curve as defined in the standard EN 9073-3. According to Laplace's law, the elongation to be carried out corresponds to the desired pressure.

In order to appropriately put the bandage in place, the bandages were calibrated using a stencil, as described in the patent application WO 2007/113430, page 13, line 18, to page 14, line 6. If necessary, the value of the percentage of elongation at being put in place was refined by a few successive tests.

Each of the bandages was put in place at a given elongation, expressed as percentage, which is shown in table 2.

The "Max. Pressure at T0" value corresponds to the first working pressure recorded immediately after putting in place and "Delta at T0" corresponds to the difference in pressure between the first working pressure and the first resting pressure which are recorded immediately after putting in place. The "Max. Pressure at T24" and "Delta at T24" values correspond to the measurements recorded 24 hours after putting in place. The difference in each of these two values between T0 and T24 hours, "Max. Pressure (T0-T24)" and "Delta (T0-T24)", was then calculated.

The loss in working pressure at 24 hours, "Loss in Max. Pressure T24", with respect to the working pressure at being put in place, was also calculated by determining the ratio of the variation "Max. Pressure (T0-T24)" to the "Max. Pressure at T0".

The performance of the bandages according to the invention was compared with the bilayer compression systems sold by Urgo Limited under the K2® and K2 Lite® names. The bandages of these commercial products were already calibrated.

The combined results have been given in table 2.

TABLE 2

| Example | Elongation at being put in place | Max. Pressure at T0 | Delta at T0 | Max. Pressure at 24 h | Delta at 24 h | Delta (T0-T24) | Pressure (T0-T24) | Loss in Max. Pressure at T24 h |
|---|---|---|---|---|---|---|---|---|
| Ktech ® | 55% | 31 | 15 | 23 | 12 | 3 | 8 | 25.8% |
| K2 ® | 55% + 50% | 44 | 19 | 35 | 17 | 2 | 9 | 20.4% |
| K2 Lite ® | 50% + 50% | 33 | 10 | 25 | 8 | 2 | 8 | 24.2% |
| 1 | 30% | 77 | 28 | 67 | 30 | −2 | 10 | 12.9% |
| 2 | 30% | 87 | 32 | 76 | 34 | −2 | 11 | 12.6% |
| 3 | 30% | 69 | 15 | 58 | 16 | −1 | 11 | 15.9% |
| 4 | 30% | 34 | 12 | 34 | 16 | −4 | 0 | 0% |
| 5 | 30% | 42 | 8 | 37 | 13 | −5 | 5 | 11.9% |
| 6 | 30% | 45 | 13 | 44 | 16 | −3 | 1 | 2.2% |
| 4 + Kpress ® | 30% + 50% | 63 | 18 | 53 | 21 | −3 | 10 | 15.9% |

INTERPRETATION OF THE RESULTS

The analysis of the results of table 2 demonstrates the performance of the compression bandages according to the invention.

Generally, these results show that it is possible to treat all the pathologies described above as there exists, depending on the products, a value range for the working pressure at 24 hours which varies from 34 to 76 mm of mercury.

It is also found that all these compression bandages exhibit an excellent retention, after 24 hours, of the pressure applied at being put in place. The large fall which is generally found for short-stretch bandages, of the order of 25 to 40% after 24 hours, and of the order of 20 to 25% for the bilayer systems which are the most effective, is here much lower because it is always less than 20% and generally between 10 and 15%, indeed even less than 5% for example 6 and zero for example 4.

To be able to apply a high pressure and to retain it over time is a very important parameter for the treatment of lymphedemas, in particular leg lymphedemas, for which a pressure at 24 hours of greater than 60 mm of mercury and preferably between 70 and 100 mm of mercury is desired.

Examples 1 and 2 are particularly well suited to these pathologies.

Likewise, it is found that the value for the differences in pressure at 24 hours varies between 13 and 34 mm of mercury, which makes it possible to be appropriate for all the categories of leg ulcers indicated above.

It is also found that the difference in pressure between working pressure and resting pressure does not decrease over time but on the contrary, unexpectedly, increases.

Thus, for all the bandages, the difference between the Delta after putting in place and the Delta at 24 hours is negative.

This result is all the more remarkable as it is obtained by a slower fall in the working pressure, "Max. Pressure" (which guarantees the effectiveness of the system), than that in the resting pressure.

The compression bandages according to the invention are thus the first to improve their effectiveness over time.

It may also be observed that these results are obtained with products based on different materials or assembled according to different technologies.

Thus, if a bandage is targeted which exhibits a difference in pressure at 24 hours of the order of 15 to 25 mm of mercury, the compression bandages of examples 3, 4 and 6 can meet these specifications.

Example 4 is particularly advantageous because this bandage can be used in several ways.

Thus, in order to be able to treat mixed arterial and venous ulcers, what are desired, because of the arterial component, are low working pressures of the order of 30 to 35 mm of mercury while retaining a high difference in pressure.

With the current bandages, it is very difficult to combine these two requirements. In order to obtain this result, it has thus been necessary to develop a new specific compression system, K2 Lite®.

It is found that the bandage of example 4, put in place at 30% elongation, makes it possible to obtain pressure values in the desired range and of the same order as K2 Lite® while retaining a greater difference in pressure than that of K2 Lite®.

Likewise, this bandage exhibits similar values to those of the first bandage of the K2® system, the Ktech® bandage.

If the bandage of example 6, put in place at an elongation of 30%, is combined with the second bandage KPress® of the K2® system, put in place at 50% as in the K2® system, it is found that a bilayer system is obtained with a value of difference in pressure at 24 hours which is greater than of K2®. By virtue of the use of this first bandage, a bilayer system is obtained, the effectiveness of which is improved over time since the Delta (T0-T24) is negative.

This example 4 is also noteworthy because, if the standard EN 14704-1 is applied, it is found that it is a long-stretch bandage since its elongation is 108%.

There thus exists a long-stretch bandage which exhibits a very high difference in pressure at 24 hours (16 mm of mercury) which is of the order of that of a short stretch. Furthermore, example 4 exhibits a perfect retention of the working pressure since it does not decrease; its variation is zero 0%.

All of the other examples have elongation values of less than 100% but the latter retain, indeed even increase, the difference in pressure and also the working pressure over time. Such a behavior corresponds both to a short stretch and to a long stretch.

This particularly illustrates the advantages of the nonwoven based on short and crimped fibers which cannot be used alone as compression bandage as it does not exhibit the properties of a long-stretch bandage or of a short-stretch bandage but which makes it possible to obtain, in combination with an elastic material, bandages which combine the advantages of both types of bandages without their disadvantages, all the while giving bandages having an effectiveness which improves over time, another characteristic which has never been observed.

Finally, the bandage of example 4 is advantageous because, after needling, loops of nonwoven appear at the surface of the foam which makes it possible to obtain a surface of the elastic material, in this instance the foam, which exhibits a dynamic friction coefficient of 3.87, which will reduce the sliding thereof over itself during movements.

This bandage can thus, as explained above, according to the treatment targeted, be used alone, for example over a short period of time of 1 to 3 days.

This phenomenon is encountered for all the other needled examples in which the penetration of the needles is greater than 10 mm.

For example 1 with a foam having a thickness of 4.5 mm and a penetration of the needles of 10 mm, no loop appears at the surface of the foam.

Thus, for examples 2, 5 and 6, dynamic friction coefficients of 3.58, 3.62 and 3.79 are respectively found.

The invention claimed is:

1. A compression bandage comprising an elastic material and a nonwoven of crimped fibers obtained from short conjugate fibers,
    said elastic material and said nonwoven being assembled together,
    said nonwoven having a grammage of between 70 g/m² and 300 g/m²,
    said crimped fibers being uniformly crimped in a thickness direction of the nonwoven, and exhibiting a mean curvature radius between 10 and 200 micrometers, and
    a surface of the nonwoven having between 10 and 50 crimped fibers/cm².

2. The compression bandage as claimed in claim 1, wherein the short conjugate fibers are bicomponent fibers that are made of two polymer components which exhibit a softening point greater than or equal to 100° C., and which are selected from the group consisting of polypropylene polymers, polyester polymers and polyamide polymers.

3. The compression bandage as claimed in claim 2, wherein the bicomponent fibers are composed of a first polymer which is a polyethylene terephthalate and of a second polymer which is a copolymer of an alkylene arylate with isophthalic acid and/or diethylene glycol.

4. The compression bandage as claimed in claim 2, wherein the two polymer components consist of two different aromatic polyester polymers.

5. The compression bandage as claimed in claim 1, wherein the short conjugate fibers have a mean count between 1 and 5 dtex, and a mean length between 10 and 100 mm.

6. The compression bandage as claimed in claim 1, wherein the crimped fibers exhibit a mean curvature radius between 50 and 160 micrometers.

7. The compression bandage as claimed in claim 1, wherein the nonwoven has a grammage of between 80 and 200 g/m².

8. The compression bandage as claimed in claim 1, wherein the surface of the nonwoven has between 10 and 35 crimped fibers/cm².

9. The compression bandage as claimed in claim 1, wherein the nonwoven exhibits, in a cross-section taken parallel to the thickness direction thereof,
    a fiber incurvation ratio greater than or equal to 1.3, and
    a ratio between a minimum value of the fiber incurvation ratio and a maximum value of the fiber incurvation ratio greater than 75%,
    wherein said ratio and said fiber incurvation ratio are measured in three parts of the nonwoven, each part corresponding to one third thereof in a cross-section taken perpendicular to the thickness direction of the nonwoven.

10. The compression bandage as claimed in claim 1, wherein the elastic material and the nonwoven are needled and in that the compression bandage exhibits a peel strength at 180° on itself of between 0.02 and 0.5 N/cm.

11. The compression bandage as claimed in claim 1, wherein the elastic material and the nonwoven are needled and a surface of the elastic material exhibits, after assembling, a dynamic friction coefficient of between 2 and 4.

12. The compression bandage as claimed in claim 11, wherein the elastic material is a hydrophobic or hydrophilic foam, or a 3D knitwear.

13. The compression bandage as claimed in claim 11, wherein the elastic material is a hydrophilic polyurethane foam.

14. The compression bandage as claimed in claim 1, wherein the elastic material is chosen from textile materials, cellular materials, films or their combinations.

15. The compression bandage as claimed in claim 1, wherein the nonwoven and the elastic material are assembled by needling, with an adhesive or by ultrasound.

16. The compression bandage as claimed in claim 1, wherein the nonwoven is composed of bicomponent fibers based on aromatic polyester polymers, the nonwoven has a grammage of between 90 and 150 g/m² and the surface of the nonwoven has between 10 and 35 crimped fibers/cm².

17. The use of a compression bandage as claimed in claim 1 comprising applying the compression bandage to a limb of a patient.

18. The compression bandage as claimed in claim 1, wherein the short conjugate fibers have a mean count between 1.5 and 3 dtex, and a mean length between 40 and 60 mm.

19. The compression bandage as claimed in claim 1, wherein the crimped fibers exhibit a mean curvature radius of between 70 and 130 micrometers.

20. The compression bandage as claimed in claim 1, wherein the nonwoven has a grammage of between 90 and 150 g/m².

21. The compression bandage as claimed in claim 1, wherein the elastic material and the nonwoven are needled and in that the compression bandage exhibits a peel strength at 180° on itself of between 0.025 and 0.05 N/cm.

22. The compression bandage as claimed in claim 1, wherein the elastic material and the nonwoven are needled and a surface of the elastic material exhibits, after assembling, a dynamic friction coefficient of between 2 and 3.

* * * * *